(12) United States Patent
Welker et al.

(10) Patent No.: US 8,113,070 B2
(45) Date of Patent: Feb. 14, 2012

(54) SIGHT GLASS WITH A FLOW DIRECTING ASSEMBLY

(75) Inventors: Brian H. Welker, Fulshear, TX (US);
Dennis M. McKay, Richmond, TX (US)

(73) Assignee: Welker, Inc., Sugar Land, TX (US)

( * ) Notice: Subject to any disclaimer, the term of this patent is extended or adjusted under 35 U.S.C. 154(b) by 425 days.

(21) Appl. No.: 12/484,162

(22) Filed: Jun. 12, 2009

(65) Prior Publication Data

US 2010/0313655 A1    Dec. 16, 2010

(51) Int. Cl.
*G01N 1/04* (2006.01)
(52) U.S. Cl. .................................. 73/864.73
(58) Field of Classification Search ............. 73/863.891, 73/863.86, 864.73
See application file for complete search history.

(56) References Cited

U.S. PATENT DOCUMENTS
6,818,045 B2    11/2004    Welker

*Primary Examiner* — Hezron E Williams
*Assistant Examiner* — Jamar Ray
(74) *Attorney, Agent, or Firm* — Husch Blackwell LLP

(57) ABSTRACT

A sight glass with a flow directing assembly is used to detect the presence of entrained liquids in natural gas during spot sampling procedures. The flow directing assembly directs at least a portion of the gas flow to impinge upon a first transparent window and swirl around in a chamber of the sight glass which may cause droplets of liquid to form on the inside of the window and may cause a fog to form inside the chamber, all of which make it easier to see the existence of liquids in the natural gas. At least one embodiment of this sight glass also acts as a fluid separator, collecting the liquids in the chamber which may then be periodically drained.

20 Claims, 3 Drawing Sheets

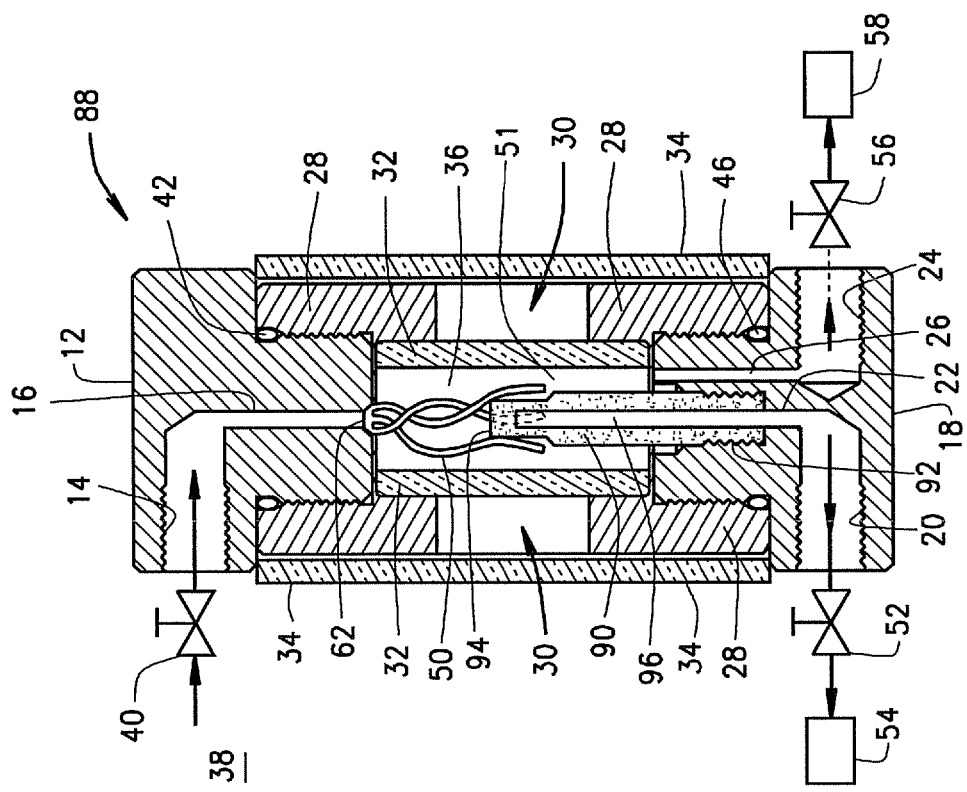

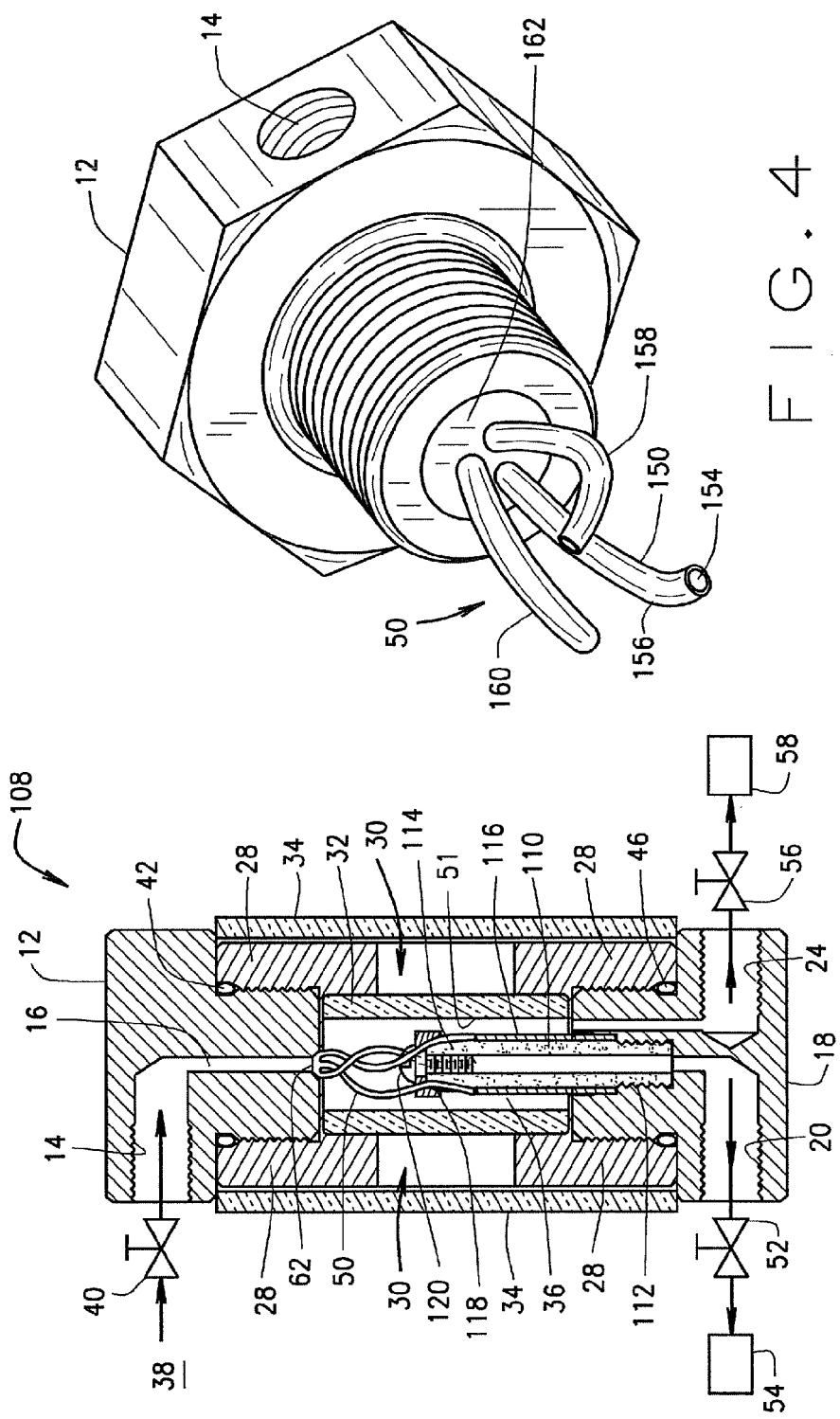

SIGHT GLASS WITH A FLOW DIRECTING ASSEMBLY

BACKGROUND OF THE INVENTION

Natural gas may be collected in a portable sample collection vessel and taken to a laboratory for analysis. This technique is often called "spot sampling" in the industry. In the laboratory, the sample is often analyzed to determine the Btu content of the natural gas using a high pressure gas chromatograph (HPGC). The HPGC is an excellent instrument for analyzing the content of a dry sample of any gas; however this instrument does not do a good job of analyzing a sample that includes fluids.

While spot sampling natural gas, it is important to determine whether the gas is dry or if it has entrained liquids, which is often referred to as "wet gas". U.S. Pat. No. 6,818,045, which is incorporated herein by reference, entitled "Liquid Separator with Integral Sight Glass" assigned to Welker Engineering Company, the predecessor of the present assignee, Welker, Inc. was an apparatus that was intended to show whether the gas was dry or wet as it passed into a sample container during a spot sampling procedure. However, in use, it was difficult for the field technician to accurately determine whether the gas was dry or wet using the apparatus disclosed in the '045 Patent. There is still a need in the industry for an economical and simple way to determine whether gas is wet or dry while spot sampling.

Welker Engineering Company has previously sold a sight glass without a filter called the model SG3. The SG3 sight glass was primarily used with odorant injection systems to provide visual confirmation that the odorant was being properly injected into the system. The SG3 was also used to provide visual confirmation in chemical injection systems that use glycol. In some situations, the SG3 has been used at a spot sampling station to visually determine if liquid was being transferred into a sample cylinder. The SG3 did not prevent liquids from entering a sample cylinder nor did it have a flow directing assembly.

Welker, Inc. has also previously sold a filter without a sight glass called the LE2. The LE2 filter has been used at spot sampling stations to keep liquids out of sample cylinders. However, the LE2 filter did not provide any visual information to the personnel that were taking the spot sample.

Other companies, such as A+ Corporation of Prairieville, La. also sell liquid separators and filters to keep liquids out of sample cylinders at spot sampling stations. Some of these products from A+ are described in the company web site (www.apluscorporation.com), but none have a flow directing assembly. In summary, the prior art filters and liquid separators from Welker and A+ do not incorporate a sight glass or a flow directing element. There is still a need in the industry for improved equipment to detect entrained liquids in natural gas.

SUMMARY OF THE INVENTION

The present invention is a sight glass to be used during spot sampling of natural gas at pressures of up to 2000 psi, to determine if the gas is wet or dry. The sight glass includes a first transparent window that in conjunction with the end caps defines a chamber through which the natural gas passes prior to being captured in a sample container. The first transparent window must be capable of withstanding the operating pressure of the natural gas that is being sampled. The flow directing assembly causes at least a portion of the natural gas to impinge upon the inside surface of the first transparent window which makes it easier to see from the outside by a sampling technician.

In one embodiment, the first transparent window is cylindrical and the flow directing assembly includes three hollow tubes that are curved causing the gas flow to impinge upon and swirl around the inside cylindrical surface of the first transparent window which in some instances causes droplets to form on the inside surface of the first transparent window when wet gas is being sampled. These droplets are conspicuous and easy to see by a spot sampling technician. The swirling action also sometimes causes a fog to form in the chamber which also is conspicuous and easy to see by a spot sampling technician.

In one embodiment, a replaceable membrane acts to separate liquid, if any, from the gas as it impinges and swirls around the chamber. In several embodiments, the chamber acts as a liquid collection vessel. From time to time, a valve may be opened to drain accumulated liquids from the chamber.

BRIEF DESCRIPTION OF THE DRAWINGS

FIG. 1 is a section of a sight glass with an open ended elongate riser tube.

FIG. 2 is a section view of an alternative embodiment of the sight glass of FIG. 1 with an elongate riser tube formed from porous sintered metal.

FIG. 3 is a section view of a sight glass of an alternative embodiment of the sight glass of FIG. 1 with a replaceable membrane filter to separate liquid, if any from the gas.

FIG. 4 is a perspective view of one embodiment of a flow directing assembly.

DETAILED DESCRIPTION OF THE INVENTION

Figure 5:
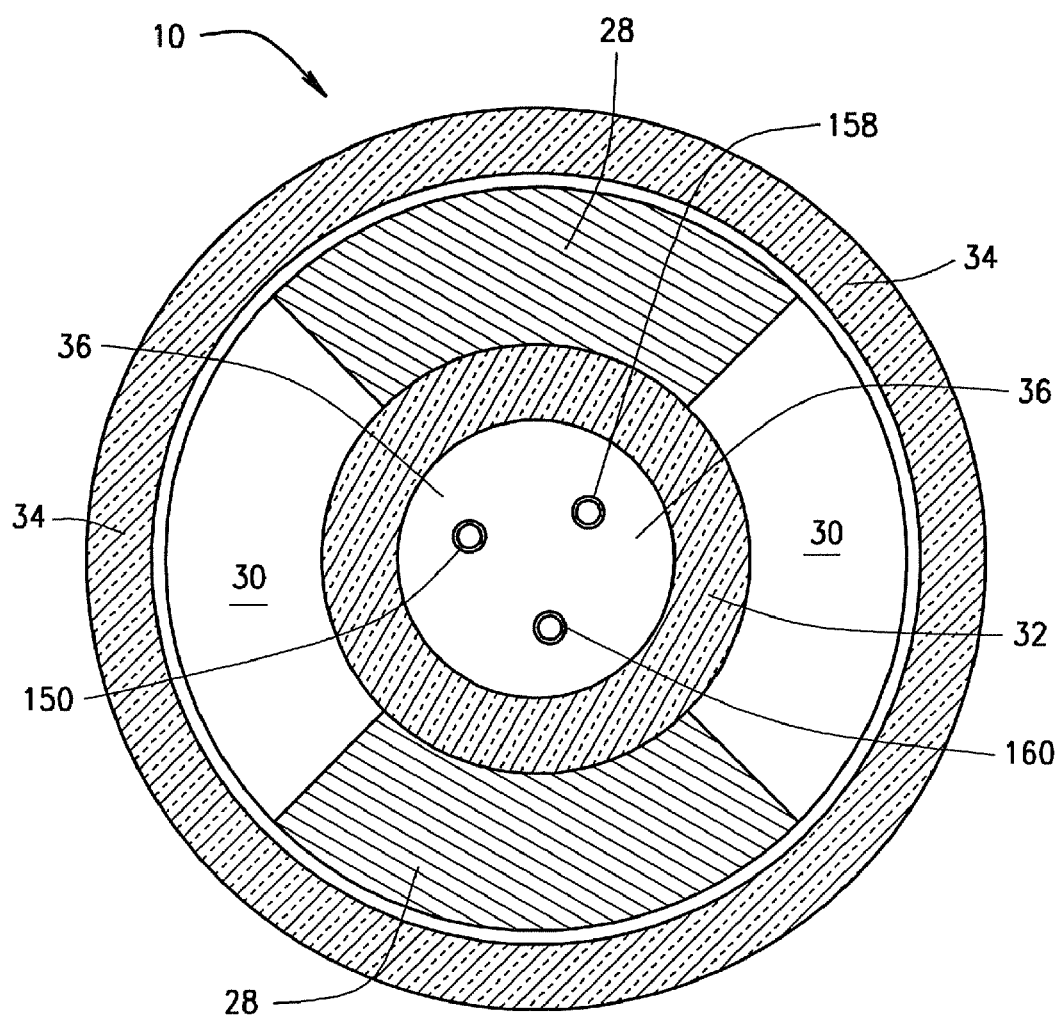
FIG. 5 is a section view of the sight glass of FIG. 1 along the line 5-5.

FIG. 1 is a section view of a sight glass generally identified by the numeral 10. A top cap 12 defines an inlet 14 and an inlet passageway 16. A bottom cap 18 defines an outlet 20 and an outlet passageway 22. The bottom cap further defines a drain 24 and a drain passageway 26. A body 28 defines a viewing slot 30. The body threadably engages the top cap and bottom cap. A first transparent window 32 is captured between the top and bottom caps. A second transparent window 34 is also captured between the top and bottom caps.

The first transparent window 32 may be formed from glass. One brand of glass that may be suitable is Gold Dot brand tempered glass from Corning of Corning, N.Y. Other brands of glass may be suitable for use in this invention provided they are capable of withstanding the operating pressure of the fluids that pass through the apparatus which may reach 2,000 psi or more. The second transparent window 34 may be formed from plastic. One brand of plastic that may be suitable for forming the second transparent window is Plexiglas® brand thermoplastic poly (methylmethacrylate)-type polymers sold by Rhom and Haas Company of Philadelphia, Pa.

In combination the top cap, bottom cap and the first transparent window define a chamber 36. Natural gas and perhaps entrained fluids from a natural gas source 38 pass through an inlet valve 40 to the inlet 14, through the inlet passageway 16 and into the chamber 36. An outside observer may look through the second transparent window 34, the viewing slot 30 and the first transparent window 32 into the chamber 36 to see whether any entrained liquids are present. An O-ring 42 seals the top cap against the body. A second O-ring 46 seals the bottom cap against the body.

The flow directing assembly 50 is in fluid communication with the inlet and the inlet passageway to direct at least a portion of the natural gas to impinge upon the inside surface 51 of the first transparent window 32 surrounding the chamber 36 to make it easier for an outside observer to detect whether there are liquids present in the natural gas. One embodiment of the flow directing assembly is better seen in FIG. 4. In FIG. 4, the flow directing assembly is angled to cause the natural gas to swirl about in the chamber which may be cylindrical as shown in FIG. 1.

In FIG. 1, the natural gas exits the chamber and passes through the outlet passageway 22, through the outlet valve 52 into a removable sample collection apparatus 54. When captured in the sample collection apparatus the natural gas and any entrained liquids are referred to in the industry as a "sample".

The removable sample collection apparatus is an off the shelf item and may be purchased in many different configurations from many different vendors, as is well known to those skilled in the art. Once filled, the sample collection apparatus may be taken to a laboratory to analyze the sample. But if the natural gas is found to have entrained liquids while the sample is being taken, it may be discarded. In the alternative, the sample collection apparatus with a wet sample will be tagged so the lab may take precautions not to injure the HPGC. Yet another alternative is to bring a portable separator to the well or other location to strip out the liquids.

In the past, it was common to build large "stripper" plants in a gas field to separate the liquids from the natural gas. As a result, most pipelines transported dry gas. Today, gas fields are smaller and large stripper plants are becoming less common. Some smaller portable separators are available, but they are not used on all wells or pipelines. Therefore, wet gas is encountered with more frequency today than in years past.

A drain valve 56 is in fluid communication with the drain passageway 26 and a liquid collecting apparatus 58. If liquids collect in the chamber 36, the drain valve 56 may be opened to drain liquids from the chamber through the drain passageway into the liquid collecting apparatus, thus discouraging liquids entering the passageway 22.

The flow directing assembly 50 is connected to the outlet port 62 of the inlet passageway 16. In this embodiment, all the natural gas that flows through the sight glass 10 also flows through the flow directing assembly 50 to better determine whether entrained liquids exist in the natural gas.

A hollow elongate riser 64 extends from the bottom cap into the chamber 36. The hollow elongate riser 64 may be integral with the bottom cap, as shown, or it may be a separate member that threadably engages the bottom cap, not shown in this figure. The proximal end 66 of the elongate riser 64 is in fluid communication with the outlet passageway 22 and the distal end 68 is in fluid communication with the chamber 36.

Natural gas flows through the inlet 14, the inlet passageway 16, and the flow directing assembly 50 into the chamber 36. In one embodiment, the natural gas impinges the inside surface 51 of the first transparent window 32 and swirls around in the chamber 36. Liquids, if any may appear on the inside surface 51 of the first transparent window 32, as droplets and/or a fog inside the chamber itself. Liquids may also be separated from the natural gas in the chamber 36. The natural gas then leaves the chamber and passes through the hollow elongate riser 64, the outlet passageway 22, the outlet 20, and the outlet valve 52 into the sample collection apparatus 54, while liquids are encouraged to exit through passageway 26.

FIG. 2 is a section view of an alternative embodiment of the sight glass 88 with an elongate riser tube 90 formed from porous sintered metal. The elongate riser tube 90 has a proximal end 92 which threadably engages the bottom cap 18. The elongate riser tube 90 has a distal end 94 which is closed. The center 96 of the elongate riser tube 90 is otherwise open and in fluid communication with the outlet passage 22. Except for the riser tube 90, the sight glass 88 of FIG. 2 is similar to the sight glass shown in FIG. 1 and common components have common numbers. The purpose of the sintered elongate riser tube 90 is to act as a particulate filter for the natural gas. The sintered elongate riser tube 90 will pass some liquids and all gases, but not particles.

FIG. 3 is a section view of an alternative embodiment of the sight glass 108 with a replaceable membrane to separate liquid, if any from the gas. The hollow sintered metallic riser 110 has an open proximal end 112 that threadably engages the bottom cap 18 and an open distal end 114. A membrane filter 116 is sized and arranged to fit over a portion of the hollow sintered metallic riser. The membrane filter may be formed from Teflon® brand tetrafluoroethylene fluorocarbon polymer produced by Du Pont de Nemours, E.I. Company. However, other membranes may be suitable in this invention provided that they achieve separation of gas from liquids. For example, Tyvek® brand material also from Du Pont may also be suitable as well as Millipore four micron filter paper from Pall Specialty materials, of Charlotte, N.C. and/or cat gut may also be suitable. The only requirement for the membrane is that it be gas permeable and impermeable to liquids. A cap 118 is sized and arranged to fit over the distal end 114 of the hollow sintered metallic riser 110 to hold the membrane filter 116 in place. A screw 120 threadably engages the distal end 114 of the hollow sintered metallic riser and captures the cap on the riser. The cap holds the membrane filter 116 in place.

FIG. 4 is a perspective view of one embodiment of a flow directing assembly generally identified by the numeral 50. A first tubular member 150 has a tubular inlet, not shown, and a tubular outlet 154 both in fluid communication with the inlet 14 and inlet passageway 16. The tubular member 150 is curved at 156 to cause the natural gas and entrained liquids, if any, to impinge upon the inside surface 51 of the first transparent window 32 to make it easier for an outside observer to see entrained liquids in the natural gas flowing through the sight glass 10, 88 or 108. The purpose of the curved tubular member 150 is to cause the natural gas and entrained liquids, if any, to impinge upon the inside surface 51 and swirl about the chamber 36. As previously mentioned in some situations, this may form droplets of liquid on the inside surface 51 and otherwise may cause a fog to appear in the chamber 36, both of which are easy to see by an outside observer.

A second tubular member 158 and a third tubular member 160 are welded together at 162 into the outlet port 62 of the inlet passageway 16. The outlet port 62 is better seen in the preceding figures. The flow directing assembly 50 includes at least one tubular member and in the preferred embodiment includes at least three tubular members, as shown in FIG. 4. The flow directing assembly directs at least a portion of the flow of natural gas from the outlet port 14; in the embodiment shown in FIG. 4 all the flow of natural gas from the outlet port 14 is being directed through the flow directing assembly 50.

FIG. 5 is a section view of the sight glass 10 of FIG. 1 along the line 5-5. The second transparent window 34 surrounds the body 28 which defines a viewing slot 30. The sampling technician looks through the second transparent window 34, through the viewing slot 30 through the first transparent window 32 into the chamber 36 to determine the presence of liquids, if any, in the natural gas. The first tubular member 150, the second tubular member 158 and the third tubular member 160 are seen in section view. The first transparent window 32 may be formed from high strength glass to withstand the pressures of the natural gas, which may reach up to 2,000 psi. The body 28 is typically formed from metal and the second transparent window may be formed from plastic and acts as a shield.

The invention claimed is:

1. A sight glass is in fluid communication with a source of natural gas and a removable sample container, the sight glass comprising:
    a body at least partially defining a chamber, the body having an inlet in fluid communication with the source of natural gas, an outlet in fluid communication with the removable sample container, and a drain;
    a first transparent window structure mounted in the body having an outside surface and an inside surface to allow an individual positioned outside the sight glass to view an interior of the chamber and the inside surface of the first transparent window structure;
    a second transparent member mounted to the body and positioned exterior of the first transparent window structure to shield the first transparent window structure; and
    a flow directing assembly in fluid communication with the inlet directing at least a portion of the flow of the natural gas to impinge against the inside surface of the first transparent window to allow an individual positioned outside the sight glass to better detect liquids in the natural gas.

2. The apparatus of claim 1 wherein the flow directing assembly includes at least one tubular member to direct the natural gas towards the inside surface of the first transparent window, the flow directing assembly being angled to cause the natural gas to swirl around the inside surface of the first transparent window to allow an individual positioned outside the sight glass to better detect liquids in the natural gas.

3. The apparatus of claim 2 wherein the flow directing assembly channels all the natural gas from the inlet towards the inside surface of the first transparent window.

4. The apparatus of claim 1 further including, an elongate riser tube in the chamber having a riser inlet in fluid communication with the chamber and a riser outlet in fluid communication with the outlet, separating liquids from the natural gas and trapping such liquids in a bottom of the chamber.

5. The apparatus of claim 4 wherein the flow directing assembly is elongate having a proximal and distal end and the distal end protruding into the chamber and the riser inlet extends beyond distal end of the flow directing assembly in the chamber, separating liquids from the natural gas and trapping such liquids in the bottom of the chamber.

6. The apparatus of claim 5 wherein the drain is in fluid communication with a valve, which is normally in a closed position, but when opened allows discharge of the separated liquid from the chamber.

7. A sight glass is in fluid communication with a source of natural gas and a removable sample container, the sight glass comprising:
    a body at least partially defining a chamber, the body having an inlet in fluid communication with the source of natural gas, an outlet in fluid communication with the removable sample container, and a drain;
    a first transparent window structure mounted in the body having an outside surface and an inside surface to allow an individual positioned outside the sight glass to view an interior of the chamber and the inside surface of the first transparent window structure;
    a second transparent member mounted to the body and positioned exterior of the first transparent window structure to shield the first transparent window structure;
    a flow directing assembly in fluid communication with the inlet directing at least a portion of the flow of the natural gas to impinge against the inside surface of the first transparent window to allow an individual positioned outside the sight glass to better detect liquids in the natural gas; and
    an elongate riser tube formed from sintered metal having a hollow center, open on the proximal end in fluid communication with the outlet and closed on the distal end.

8. The apparatus of claim 7 wherein the flow directing assembly includes at least one tubular member to direct the natural gas towards the inside surface of the first transparent window, the flow directing assembly being angled to cause the natural gas to swirl around the inside surface of the first transparent window to allow an individual positioned outside the sight glass to better detect liquids in the natural gas.

9. The apparatus of claim 8 wherein the flow directing assembly channels all the natural gas from the inlet towards the inside surface of the first transparent window.

10. The apparatus of claim 9 wherein the second transparent member includes a transparent plastic shield to protect the first transparent window structure from inadvertent damage.

11. The apparatus of claim 10 wherein a membrane formed from polytetrafluoroethylene is located in the chamber.

12. The apparatus of claim 11 wherein the drain is in fluid communication with a valve, which is normally in a closed position, but when opened allows discharge of the separated liquid from the chamber.

13. A sight glass is in fluid communication with a source of natural gas and a removable sample container, the sight glass comprising:
    a body at least partially defining a chamber, the body having an inlet in fluid communication with the source of natural gas, an outlet in fluid communication with the removable sample container, and a drain to permit removal of entrained liquids from the chamber;
    a first transparent window structure mounted in the body to allow an individual positioned outside the liquid separator to view an interior of the chamber;
    a second transparent member mounted to the body and positioned exterior of the first transparent window structure to shield said first transparent window structure;
    a flow directing assembly in fluid communication with the inlet directing at least a portion of the flow of the natural gas to impinge against the inside surface of the first transparent window to allow an individual positioned outside the sight glass to better detect liquids in the natural gas;
    a filter assembly positioned in the chamber and connected to the outlet, the filter assembly separating entrained liquids from the natural gas whereby substantially dry gas passes from the liquid separator to the removable sample container; and
    the filter assembly having a membrane that is permeable to gas and substantially impermeable to liquids.

14. The apparatus of claim 13 wherein the flow directing assembly includes at least one tubular member to direct the natural gas towards the inside surface of the first transparent window, the flow directing assembly being angled to cause the natural gas to swirl around the inside surface of the first transparent window to allow an individual positioned outside the sight glass to better detect liquids in the natural gas.

15. The apparatus of claim 14 wherein the flow directing assembly channels all the natural gas from the inlet towards the inside surface of the first transparent window.

16. A sight glass is in fluid communication with a source of natural gas and a removable sample container, the sight glass comprising:
   a body at least partially defining a chamber, the body having an inlet in fluid communication with the source of natural gas, an outlet in fluid communication with the removable sample container, and a drain;
   a first transparent window structure mounted in the body having an outside surface and an inside surface to allow an individual positioned outside the sight glass to view an interior of the chamber and the inside surface of the first transparent window structure;
   a second transparent member mounted to the body and positioned exterior of the first transparent window structure to shield the first transparent window structure;
   a flow directing assembly in fluid communication with the inlet directing at least a portion of the flow of the natural gas to impinge against the inside surface of the first transparent window to allow an individual positioned outside the sight glass to better detect liquids in the natural gas;
   a filter assembly positioned in the chamber and connected to the outlet, the filter assembly separating entrained liquids from the natural gas whereby substantially dry gas passes from the liquid separator to the removable sample container;
   the filter assembly having;
      a membrane that is permeable to gas and substantially impermeable to liquids and
      a porous elongate riser tube to support the membrane.

17. The apparatus of claim 16 wherein the flow directing assembly includes at least one tubular member to direct the natural gas towards the inside surface of the first transparent window, the flow directing assembly being angled to cause the natural gas to swirl around the inside surface of the first transparent window to allow an individual positioned outside the sight glass to better detect liquids in the natural gas.

18. The apparatus of claim 17 wherein the flow directing assembly channels all the natural gas from the inlet towards the inside surface of the first transparent window.

19. The apparatus of claim 18 wherein the membrane is formed from polytetrafluoroethylene.

20. The apparatus of claim 19 wherein the porous elongate riser tube supports the membrane and is formed from sintered metal.

\* \* \* \* \*